US008144315B2

(12) United States Patent
Cranch et al.

(10) Patent No.: US 8,144,315 B2
(45) Date of Patent: Mar. 27, 2012

(54) METHOD AND APPARATUS FOR CHARACTERIZING A MULTILAYERED STRUCTURE

(75) Inventors: Geoffrey A. Cranch, Fairfax Station, VA (US); Gordon M. H. Flockhart, Glasgow (GB)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 126 days.

(21) Appl. No.: 12/757,075

(22) Filed: Apr. 9, 2010

(65) Prior Publication Data
US 2010/0271623 A1 Oct. 28, 2010

Related U.S. Application Data

(60) Provisional application No. 61/171,856, filed on Apr. 23, 2009.

(51) Int. Cl.
*G01N 21/00* (2006.01)
(52) U.S. Cl. .................................................. 356/73.1
(58) Field of Classification Search ........................ None
See application file for complete search history.

(56) References Cited

U.S. PATENT DOCUMENTS

| | | | |
|---|---|---|---|
| 5,104,222 A | 4/1992 | Kersey et al. | |
| 5,644,664 A | 7/1997 | Burns et al. | |
| 7,062,173 B2 * | 6/2006 | Tomofuji et al. | 398/82 |
| 7,194,163 B2 | 3/2007 | Stepanov | |
| 7,263,871 B2 | 9/2007 | Selker et al. | |
| 7,450,239 B2 * | 11/2008 | Uehara et al. | 356/451 |

OTHER PUBLICATIONS

R. Feced, and M. N. Zervas, "Effects of random phase and amplitude errors in optical fiber Bragg gratings," J. of Lightw. Technol., vol. 18, No. 1, pp. 90-101 (2000).
T. Erdogan, "Fiber grating spectra" J. Lightw. Technol., vol. 15, No. 8, pp. 1277 1294 (1997).
P. Giaccari, H. G. Limberger, and R. P. Salathe, "Local coupling-coefficient characterization in fiber Bragg gratings," Optics Letters, vol. 28, No. 8, pp. 598-600 (2003).
X. Chapeleau, D. Leduc, C. Lupi, F. Lopez-Gejo, M. Douay, R. Le Ny, and C. Boisrobert, "Local characterization of fiber-Bragg gratings through combined use of low-coherence interferometry and a layer-peeling algorithm," Applied Optics, vol. 45, No. 4, pp. 728 735 (2006).
O. H. Waagaard, "Spatial characterization of strong fiber Bragg gratings using thermal chirp and optical-frequency domain reflectometry", J. Lightw. Technol., vol. 23, No. 2, pp. 909-914 (2005).

(Continued)

*Primary Examiner* — Tu Nguyen
(74) *Attorney, Agent, or Firm* — Amy Rossing; Joslyn Barritt

(57) ABSTRACT

An apparatus and method for characterizing the complex coupling coefficient of a multilayered periodic structure either during or after inscription is described. This apparatus is capable of continuously measuring the complex reflectivity at single or multiple wavelengths to a resolution limited by Rayleigh scattering in the waveguide section where the structure is inscribed. The apparatus is also capable of rejecting undesired signals associated with stray reflections in the system and unwanted environmentally induced change in optical path lengths during the inscription procedure. The complex coupling coefficient of the multilayered periodic structure can be derived from the measured complex reflectivity and can reveal errors present in the structure. The complex coupling coefficient can also be used to derive an error signal to enable implementation of a closed loop inscription system capable of inscribing error free multilayer structures.

18 Claims, 8 Drawing Sheets

OTHER PUBLICATIONS

P. A. Krug, R. Stolte, and R. Ulrich, "Measurement of index modulation along an optical fiber Bragg grating," Optics Letters, vol. 20, No. 17, pp. 1767-1769 (1995).

F. Ei-Diasty, A. Heaney, and T. Erdogan, "Analysis of fiber Bragg gratings by a side-diffraction interference technique," Applied Optics, vol. 40, No. 6, pp. 890-896 (2001).

I. Petermann, S. Helmfrid, and A. T. Friberg, "Limitations of the interferometric side diffraction technique for fibre Bragg grating characterization," Optics Communications 201 (2002) 301-308.

I. Petermann, S. Helmfrid, and P. Y. Fonjallaz, "Fibre Bragg grating characterization with ultraviolet-based . interferometric side diffraction," J. Opt. A: Pure Appl. Opt. 5 (2003) 437-441.

J- Canning, M. Janos, D. Y. Stepanov, and M. G. Sceats, "Direct measurement of grating chirp using resonant side scatter spectra," Electronics Letters, vol. 32, No. 17, pp. 1608-1610 (1996).

J. Canning, D. C. Psaila, Z. Brodzeli, A. Higley, and M. Janos, "Characterization of apodized fiber Bragg gratings for rejection filter applications", Applied Optics, vol. 36, No. 36, pp. 9378-9382 (1997).

C. J. S. de Matos, P. Torres, L. C. G. Valente, W. Margulis, and R. Stubbe, "Fiber Bragg grating (FBG) characterization and shaping by local pressure," J. of Lightw. Technol., vol. 19, No. 8, pp. 1206-1211 (2001).

N. Roussel, S. Magne, C. Martinez, and P. Ferdinand, "Measurement of index modulation along fiber Bragg gratings by side scattering and local heating techniques," Optical Fiber Technology 5, 119-132 (1999).

E. Brinkmeyer, G. Stolze, D. Johlen, "Optical space domain reflectometry (OSDR) for determination of strength and chirp distribution along optical fiber gratings" Proc. OSA Conf. Bragg Gratings 1996, (Photosensitivity and Poling in Glass Waveguides (BGPP) 1997), paper BsuC2-1, p. 33.

I. G. Korolev, S. A. Vasil'ev, O. I. Medvedkov, and E. M. Dianov, "Study of local properties of fibre Bragg gratings by the method of optical space-domain reflectometry," Quantum Electronics 33(8), 704 710 (2003).

D. Stepanov, G. Edvell, and M. Sceats, "Monitoring of the fiber Bragg grating fabrication process," in Optical Fiber Communication Conference, Technical Digest (CD) (Optical Society of America, 2004), paper ThC1.

S. Kieckbusch, Ch. Knathe, and E. Brinkmeyer, "Fast and Accurate Characterization of Fiber Bragg Gratings with High Spatial and Spectral Resolution", OFC 2003, vol. 1, p. 379 (2003).

G. A. Cranch and G. A. Miller, "Improved implementation of optical space domain reflectometry for characterizing the complex coupling coefficient of strong fiber Bragg gratings" Applied Optics, vol. 48, No. 22, pp. 4506-4513 (2009).

M. J. Cole, W. H. Loh, R. I. Laming, M. N. Zervas and S. Barcelos, "Moving fibre/phase mask-scanning beam technique for enhanced flexibility in producing fibre gratings with uniform phase mask", Electronics Letters, vol. 31, No. 17, pp. 1488-1490 (1995).

J. Martin, F. Ouellette, "Novel writing technique of long and highly reflective in-fibre gratings," Electronics Letters, vol. 30, No. 10, pp. 811-812 (1994).

G. Meltz, W. W. Morey, W. H. Glenn, "Formation of Bragg gratings in optical fibers by a transverse holographic method," Optics Letters, vol. 14, No. 15, pp. 823-825 (1989).

G. M. H. Flockhart, G. A. Cranch, and C. K. Kirkendall, "Rapid characterization of the ultraviolet induced fiber Bragg grating complex coupling coefficient as a function of irradiance and exposure time" Applied Optics, vol. 46, No. 34, pp. 8237-8243 (2007).

G. A. Miller, C. G. Askins, G. A. Cranch, and E. J. Friebele "Early Index Growth in Germanosilicate Fiber Upon Exposure to Continuous-Wave Ultraviolet Light" J. Lightw Tech, vol. 25, No. 4, pp. 1034-1044 (2007).

A. Dandridge, A. B. Tveten, and T. G. Giallorenzi, "Homodyne demodulation scheme for fiber optic sensors using phase generated carrier," IEEE Journal of Quantum Electronics, vol. 18, No. 10, pp. 1647-1653 (1982).

J. Skaar, "Synthesis and characterization of fiber Bragg gratings" PhD Thesis, The Norwegian University of Science and Technology, chapter 2, Nov. 2000.

Vladimir Goloborodko, Shay Keren, Amir Rosenthal, Boris Levit, and Moshe Horowitz, Measuring temperature profiles in high-power optical fiber components, Journal of Applied OptiCS, vol. 42, No. 13 (2003), pp. 2284-2288.

International Search Report and Written Opinion dated Jun. 15, 2010 in PCT Application No. US20101030460.

\* cited by examiner

METHOD AND APPARATUS FOR CHARACTERIZING A MULTILAYERED STRUCTURE

CROSS-REFERENCE

This application claims the benefit of priority based on U.S. Provisional Patent Application No. 61/171,856 filed on Apr. 23, 2009, the entirety of which is hereby incorporated by reference into the present application.

TECHNICAL FIELD

The present invention relates to the characterization of high reflectivity multilayered structures, to characterization of multilayered structures during inscription of the multilayered structure, and to inscription of a multilayered structure with a well defined coupling coefficient.

BACKGROUND

Multilayered structures such as fiber Bragg gratings (FBG) are used in a diverse range of applications in telecommunication systems, fiber optic sensors and fiber lasers. It is well known that their performance in these applications is strongly affected by their reflectivity and dispersion characteristics. However, during their inscription, instabilities in the UV fringe pattern and imperfections in the medium containing the FBG can induce errors in the periodic structure written into the medium. The existence of such errors in the phase and amplitude of the refractive index modulation forming the grating can cause significant deviation of these characteristics from the target or required characteristics. See R. Feced, and M. N. Zervas, "Effects of random phase and amplitude errors in optical fiber Bragg gratings," *J. of Lightw. Technol.*, Vol. 18, No. 1, pp. 90-101 (2000). These errors are usually imparted during the writing process. Consequently, methods to characterize the refractive index profile of the Bragg grating post-inscription are extremely desirable to help understand the source of these errors, assist in optimization of the FBG inscription process, and provide quality control.

Techniques to characterize the spatial profile of FBGs post-inscription can be divided into the following groups: (a) swept frequency or low coherence interferometry and layer peeling, (b) side-scattering and (c) local perturbation (i.e. heat or stress) methods. None of these techniques are capable of characterizing all grating types. Thus, each has to be judged on its own merits when attempting to characterize a given FBG.

The spatial profile of the grating is described by its complex coupling coefficient $q(z)$. See T. Erdogan, "Fiber grating spectra" *J. Lightw. Technol.*, Vol. 15, No. 8, pp. 1277-1294 (1997). The coupling coefficient $q(z)$ is difficult to measure or calculate directly, so methods have been developed to calculate it indirectly. For example, swept frequency methods such as optical frequency domain reflectometry (OFDR) and low coherence methods such as optical low-coherence reflectometry measure the impulse response of the grating, which is used with an inverse scattering technique such as layer peeling to reconstruct the complex coupling coefficient of the grating. See P. Giaccari, H. G. Limberger, and R. P. Salathe, "Local coupling-coefficient characterization in fiber Bragg gratings," *Optics Letters*, Vol. 28, No. 8, pp. 598-600 (2003); and X. Chapeleau, D. Leduc, C. Lupi, F. Lopez-Gejo, M. Douay, R. Le Ny, and C. Boisrobert, "Local characterization of fiber-Bragg gratings through combined use of low-coherence interferometry and a layer-peeling algorithm," *Applied Optics*, Vol. 45, No. 4, pp. 728-735 (2006).

These methods are capable of achieving very high spatial resolution measurements (<100 μm). However, these techniques will always fail as the grating strength increases (qL>~4) such that the on-resonance penetration depth of the incident optical field is not sufficient to provide an adequate signal-to-noise ratio for the recursive reconstruction algorithm to be stable. By applying a well controlled thermally induced chirp to the grating, the use of these techniques has been extended to stronger gratings with $\bar{q}L=8.25$. See O. H. Waagaard, "Spatial characterization of strong fiber Bragg gratings using thermal chirp and optical-frequency-domain reflectometry", *J. Lightw. Technol.*, Vol. 23, No. 2, pp. 909-914 (2005). However, an upper limit still remains due to practical limitation of the thermal gradient that can be applied to the grating (~150K).

The side scattering technique measures the diffracted power from the grating when illuminated from the side and is well suited to characterizing highly chirped gratings such as dispersion compensators. This technique is capable of measuring the amplitude of the refractive index modulation, P. A. Krug, R. Stolte, and R. Ulrich, "Measurement of index modulation along an optical fiber Bragg grating," *Optics Letters*, Vol. 20, No. 17, pp. 1767-1769 (1995), and its phase, F. El-Diasty, A. Heaney, and T. Erdogan, "Analysis of fiber Bragg gratings by a side-diffraction interference technique," *Applied Optics*, Vol. 40, No. 6, pp. 890-896 (2001); I. Petermann, S. Helmfrid, and A. T. Friberg, "Limitations of the interferometric side diffraction technique for fibre Bragg grating characterization," *Optics Communications* 201 (2002) 301-308, but requires careful alignment and a high quality fiber surface to obtain reliable phase data. To date, reproducibility errors of 2-5% for the amplitude and 10°-20° for the phase have been reported. I. Petermann, S. Helmfrid, and P. Y. Fonjallaz, "Fibre Bragg grating characterization with ultraviolet-based interferometric side diffraction," *J. Opt. A: Pure Appl. Opt.* 5 (2003) 437-441. These errors can be reduced by spatially averaging the measurement at the expense of a reduced spatial resolution (few mm).

A second type of side-scattering method measures the Rayleigh scattered power radiated from the side of the grating when interrogated through the core. J. Canning, M. Janos, D. Y. Stepanov, and M. G. Sceats, "Direct measurement of grating chirp using resonant side scatter spectra," *Electronics Letters*, Vol. 32, No. 17, pp. 1608-1610 (1996); J. Canning, D. C. Psaila, Z. Brodzeli, A. Higley, and M. Janos, "Characterization of apodized fiber Bragg gratings for rejection filter applications", *Applied Optics*, Vol. 36, No. 36, pp. 9378-9382 (1997). However, a detailed analysis of this second side-scattering method has not been presented to date.

Perturbation methods involve locally modifying the refractive index of the fiber in a controlled way. This causes a change in the FBG's spectral properties, which are measured in some way and related to the grating properties at the location of the perturbation. The perturbation can be applied by a local pressure, see C. J. S. de Matos, P. Torres, L. C. G. Valente, W. Margulis, and R. Stubbe, "Fiber Bragg grating (FBG) characterization and shaping by local pressure," *J. of Lightw. Technol.*, Vol. 19, No. 8, pp. 1206-1211 (2001); by scanning a heated wire, see N. Roussel, S. Magne, C. Martinez, and P. Ferdinand, "Measurement of index modulation along fiber Bragg gratings by side scattering and local heating techniques," *Optical Fiber Technology* 5, 119-132 (1999); by scanning the fiber with a He—Ne laser, see E. Brinkmeyer, G. Stolze, D. Johlen, "Optical space domain reflectometry (OSDR) for determination of strength and chirp distribution along optical fiber gratings" *Proc. OSA Conf Bragg Gratings 1996*, (Photosensitivity and Poling in Glass Waveguides (BGPP) 1997), paper BsuC2-1, p. 33; or by scanning the fiber with a CO2 laser, see I. G. Korolev, S. A. Vasil'ev, O. I. Medvedkov, and E. M. Dianov, "Study of local properties of fibre Bragg gratings by the method of optical space-domain reflectometry," *Quantum Electronics* 33(8), 704-710 (2003). Physical contact with the fiber is likely to affect its mechanical integrity, thus non-contact methods such as those using a carbon dioxide ($CO_2$) laser are preferable.

Of these heat scan techniques, the method of optical space domain reflectometry (OSDR) has many favorable attributes. It is capable of extracting the complex coupling coefficient of the grating from a measurement at a single wavelength; it requires only to heat the grating by a few degrees Kelvin, which can be implemented with a focused beam from a CO2 laser, see Korolev, et al., supra, and does not require any complex alignment of the fiber other than to align the heating beam. Previous implementations of this technique, however, have yielded poor accuracy of the measurement. See Brinkmeyer, et al., supra and Korolev, et al., supra.

In addition, although characterization of the refractive index profile of the Bragg grating post-inscription can aid in understanding the source of inscription errors, assist in optimization of the FBG inscription process, and provide quality control, characterization of the multilayered structure during the inscription process (i.e. real time, in-situ monitoring) is even more desirable, as it can enable implementation of a closed loop inscription system which can prevent errors from building up, yielding an error-free structure from the outset. Thus, in order to achieve error free periodic structures written into the media, it is desirable to perform an in-situ measurement of the multilayered structure during the inscription procedure.

The basic concept of using interferometry to track the complex reflectivity of a multilayered structure and reconstruct the local coupling coefficient has been suggested in, for example, U.S. Pat. No. 7,194,163 to Stepanov, "Multilayered structure characterization"; and D. Stepanov, G. Edvell, and M. Sceats, "Monitoring of the fiber Bragg grating fabrication process," in *Optical Fiber Communication Conference*, Technical Digest (CD) (Optical Society of America, 2004), paper ThC1. However, the methods published therein fail to show how the interferometric measurement can reject spurious signals due to parasitic cavities present in all interferometric configurations or how they can achieve sufficient sensitivity to resolve to the level of Rayleigh scattering. Furthermore, the published method for reconstructing the coupling coefficient from the complex reflectivity from a linearly proportional relationship between these two quantities has been shown to be invalid in almost all practical situations. Other interferometric methods are capable of measuring the complex reflectivity to the limit of Rayleigh scattering while rejecting signals from spurious reflections such as Optical Frequency Domain Reflectometry (OFDR). See, e.g., S. Kieckbusch, Ch. Knathe, and E. Brinkmeyer, "Fast and Accurate Characterization of Fiber Bragg Gratings with High Spatial and Spectral Resolution", OFC 2003, vol. 1, p. 379 (2003). However, these methods gather far more data than is necessary to implement the above technique and therefore are considerably slower. Also, since OFDR requires a scanned laser source, it is not a continuous measurement, and thus is not capable of tracking the spectral phase of the multilayered structure.

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter. Instead, it is merely presented as a brief overview of the subject matter described and claimed herein.

The present invention provides an apparatus and a method for characterizing a multilayered periodic structure such as a fiber Bragg grating (FBG).

It is well known to those skilled in the art that in an FBG, the amplitude of the complex coupling coefficient is linearly related to the amplitude of the periodic variation of the refractive index along the optical fiber that forms the multilayered structure. The phase of the coupling coefficient is related to changes in periodicity of the refractive index variation, discrete phase changes or changes in background refractive index of the medium. Thus, the complex coupling coefficient of the multilayered structure will also provide a measure of the presence or absence of defects in the multilayered structure that can affect the performance of the device.

One embodiment of the invention includes an apparatus and method for characterizing the coupling coefficient of an existing high reflectivity multi-layer structure. In accordance with this embodiment of the present invention, the complex reflectivity $r(\delta)$ at a single wavelength is monitored while a weak physical perturbation is scanned along the multilayered structure. This weak perturbation may be generated by the temperature change caused when light from a laser is scanned along the multilayered structure or may be generated by applying a local pressure or transverse compression to the fiber. The complex coupling coefficient $q(z)$ can then be calculated from the measured complex reflectivity. This characterization would be carried out after inscription of the multilayered structure.

Another embodiment of the invention includes an apparatus and a method for actively monitoring the coupling coefficient of a multilayered structure such as a fiber Bragg grating while it is being inscribed. In accordance with this embodiment of the present invention, the complex reflectivity $r(\delta)$ of the multilayered periodic structure is monitored as the structure is being formed layer-by-layer and its complex coupling coefficient $q(z)$, which describes the multilayered structure, is calculated. In the case of a FBG, this may involve scanning a holographic interference pattern formed by a laser along the length of an optical fiber. The complex reflectivity is monitored as the laser is translated along the optical fiber.

The measured value of the complex coupling coefficient $q(z)$ is then compared to the pre-determined noise-free target structure. Any deviation of the measured coupling coefficient from the target structure caused by errors forming in the multilayered structure will result in a non-zero value. Integration of this quantity yields an error signal. The error signal is then used to form a closed loop inscription system which prevents the buildup of these errors. It is important to note that this method does not correct for errors after they have occurred but instead prevents them from building up.

The present invention also provides a high resolution interferometric method suitable for continuously measuring the complex reflectivity free from environmentally induced drift.

DETAILED DESCRIPTION

The aspects and features of the present invention summarized above can be embodied in various forms. The following description shows, by way of illustration, combinations and configurations in which the aspects and features can be put into practice. It is understood that the described aspects, features, and/or embodiments are merely examples, and that one skilled in the art may utilize other aspects, features, and/or embodiments or make structural and functional modifications without departing from the scope of the present disclosure.

In a first embodiment of the present invention, a multilayered periodic structure can be characterized after it has been inscribed to determine the presence of errors in the structure that may adversely affect performance. In a second embodiment of the present invention, a periodic multilayered structure can be monitored and evaluated in-situ as it is being formed layer-by-layer to minimize errors in the periodic structure that can adversely affect performance before they become part of the final structure.

Figure 1:
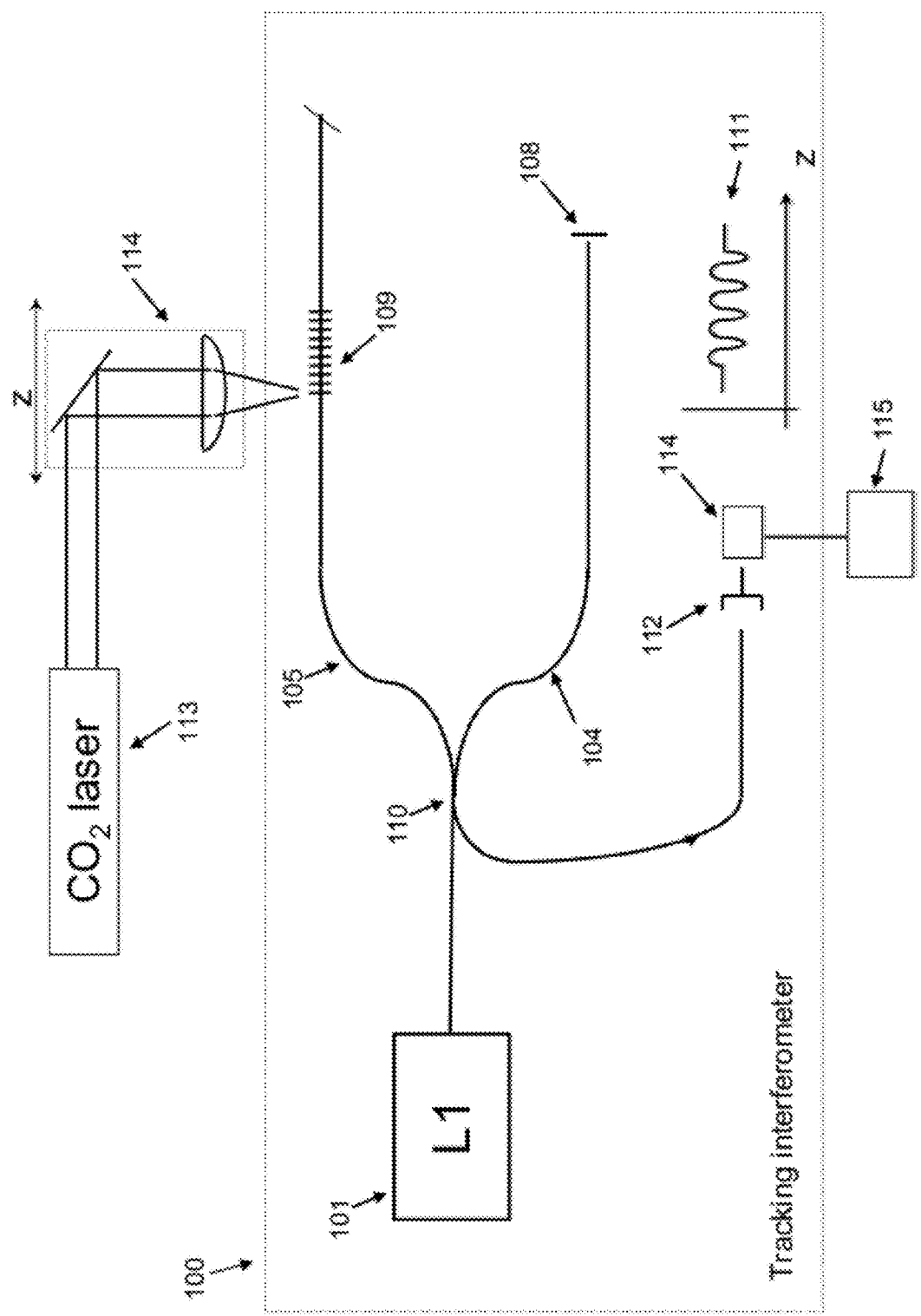
FIG. 1 depicts an exemplary embodiment of an apparatus for characterizing a multilayered structure in accordance with the present invention.

FIG. 1 illustrates an exemplary embodiment of an apparatus that can be used in the first embodiment of the present invention.

In the exemplary embodiment shown in FIG. 1, the output of a laser 101 is injected into a fiber-optic interferometer 100 formed with a direction coupler 110. The light is split into two optical fiber arms 104 and 105. One arm is connected to the multilayered structure 109 being characterized. The other arm is terminated with a reflector 108. The wavelength of the laser is set to be close to the resonance of the multilayered structure. The output interference pattern 111 of the fiber-optic interferometer, which is related to the complex reflectivity of the multilayered structure, is detected on a photodiode 112. In accordance with the present invention, a perturbation is scanned along the multilayered structure 109. The perturbation can be generated by a focused beam from a laser such as $CO_2$ laser 113, which is passed through a lens mounted on a translation stage 114. The beam is absorbed by the optical fiber in arm 105 having multilayered structure 109, locally changing its temperature. As the heat perturbation is scanned along multilayered structure 109, small changes in the interference pattern 111 due to changes in the complex reflectivity of the multilayered structure are observed. The interference pattern can be digitized, for example, by analog-to-digital converter 114 which is operationally coupled to photodiode 112, for processing by computer 115 to recover the complex coupling coefficient. As described in more detail below, the changes in the complex reflectivity are related to the coupling coefficient at the current position of the heat perturbation, and therefore, scanning the heat perturbation along the length of the multilayered structure and measuring the resulting complex reflectivity enables the coupling coefficient of the entire structure to be reconstructed as described below. Measurement of the complex reflectivity is not limited by the strength of the multilayered structure and thus the method in accordance with the present invention can be used to reconstruct the coupling coefficient of even very strong or high reflectivity fiber Bragg gratings.

Figure 2:
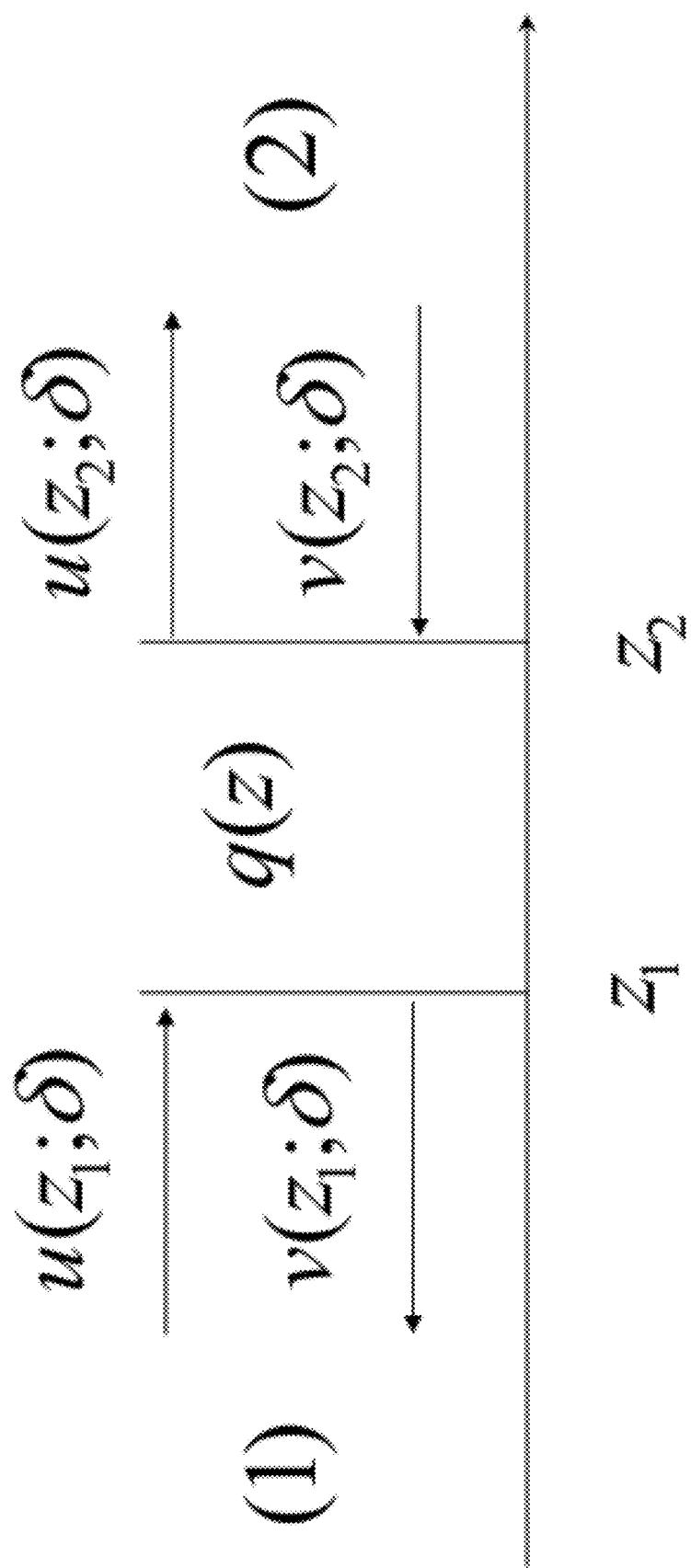
FIG. 2 depicts the relationship between the forward and backward propagating fields for a linearly polarized field propagating in an isotropic medium in the z-direction.

Optical field propagation in a periodically perturbed waveguide that includes a periodic grating structure such as a fiber Bragg grating can be described with coupled mode theory. See Erdogan, et al., supra; see also J. Skaar, "Synthesis and characterization of fiber Bragg gratings" PhD Thesis, The Norwegian University of Science and Technology, chapter 2, November 2000. For the case of a linearly polarized field propagating in an isotropic medium in the z-direction, the relationship between the forward and backward propagating fields $u(z,\delta)$ and $v(z,\delta)$ such as those illustrated in FIG. 2 is given by the coupled mode equations (1) and (2):

$$\frac{du}{dz} = i\delta u + q(z)v \quad (1)$$

$$\frac{dv}{dz} = -i\delta v + q^*(z)u \quad (2)$$

In Equations (1) and (2), q(z) is the complex coupling coefficient of the periodic grating structure, q*(z) is the complex conjugate of q(z), δ is the wavenumber detuning which is related to the Bragg wavelength of the grating by the relation $$\delta = 2\pi n \cdot \left(\frac{1}{\lambda} - \frac{1}{\lambda_B}\right),$$

n is the effective refractive index of the fiber, c is the light velocity in a vacuum, and $\lambda_B$ is the Bragg wavelength. The wavenumber detuning δ represents a normalized optical frequency (where frequency $$\nu = \frac{c}{\lambda}\Big),$$

and will be used throughout the present disclosure instead of frequency or wavelength to refer to the optical frequency. The wavenumber detuning δ is zero at a frequency corresponding to the Bragg wavelength.

The strength of the periodic grating can be quantified with an integrated coupling coefficient defined by $$\bar{q}L = \int_0^L q(z)dz \quad (3)$$

where q(z) is the complex coupling coefficient of the periodic grating described above and L is the grating length.

For the case of diminishing interaction of the incident field with the periodic structure, the solutions to the coupled mode Equations (1) and (2) reduce to $u=u_0\exp(i\delta z)$ and $v=0$. Substituting the expression for u into Equation (2) and solving the resulting first-order linear differential equation yields a simplified relationship, known as the first Born approximation, between the complex reflectivity $r(\delta)=v(0)/u(0)$ and coupling coefficient q(z), where $$r(\delta) = -\int_0^\infty q^*(z)\exp(2i\delta z)\,dz \qquad (4)$$

This approximation becomes exact in the limit of $q\to 0$ or $\delta\to\infty$. It is this later regime that can be utilized to implement a so-called off-resonance characterization of the grating, which permits use of the Born approximation even for large q, so long as it is applied in a spectral region of weak interaction.

A local phase perturbation described by the function $\phi_0(z)$, for example, a perturbation caused by a focused beam from laser 113 shown in FIG. 1, can be applied to the coupling coefficient and scanned across the grating. The evolution of the complex reflectivity of the perturbed grating $\tilde{r}(\delta_m;z')$ as a function of the perturbation position z' at a measurement wavenumber detuning $\delta_m$ far from the Bragg resonance can be described using Equation (4):

$$\tilde{r}(\delta_m;z') = -\int_0^\infty q^*(z)\cdot\exp(-i\phi_0(z-z'))\cdot\exp(2i\delta_m z)\,dz \qquad (5)$$

For the special case where the phase perturbation is small, i.e., $\phi_0\ll 1$, Equation (5) can be simplified by using the small angle approximation $\exp(i\phi_0(z))\cong 1+i\phi_0(z)$ to produce the following Equation (6):

$$\tilde{r}(\delta_m;z') = r(\delta_m) + i\int_0^\infty q^*(z)\cdot\phi_0(z-z')\cdot\exp(2i\delta_m z)\,dz \qquad (6)$$

The coupling coefficient of interest, q(z), is contained in the second term of Equation (6). Since the first term is a constant, the rate of change of the complex reflectivity with perturbation position thus yields a function closely related to the coupling coefficient. Taking the spatial derivative of $\tilde{r}(\delta_m;z')$ yields $$\frac{d\tilde{r}(\delta_m;z')}{dz'} = 2i\eta\frac{2\pi}{\lambda}\frac{\partial n}{\partial T}\int_0^\infty q^*(z)\cdot\Delta T(z-z')\cdot\exp(2i\delta_m z)\,dz \qquad (7)$$

where $\partial n/\partial T$ is the thermo-optic coefficient of the fiber and $\eta$ is the mode overlap factor.

The following relation was used to derive Equation (7) from Equation (6):

$$\frac{d\phi_0(z-z')}{dz'} = 2\eta\frac{2\pi}{\lambda}\frac{\partial n}{\partial T}\Delta T(z-z') \qquad (8)$$

where $\Delta T(z)$ is the spatially varying temperature perturbation. This relation is derived from the definition of the argument of the coupling coefficient q(z), i.e., $\arg(q(z))=-(4\eta\pi/\lambda)\cdot\int_0^z \Delta n_{dc}(z')dz'$, where $\Delta n_{dc}(z)=\partial n/\partial T\cdot\Delta T(z)$ is the direct current component of the change in refractive index n.

The integral term in Equation (7) resembles a cross-correlation integral and thus can be expressed as a convolution of the complex coupling coefficient $q^*(z)\cdot\exp(2i\delta_m z)$ with the temperature perturbation $\Delta T(-z)$:

$$\frac{d\tilde{r}(\delta_m;z')}{dz'} = 2i\eta\frac{2\pi}{\lambda}\frac{\partial n}{\partial T}\cdot\{q^*(z)\cdot\exp(2i\delta_m z)\otimes\Delta T(-z)\} \qquad (9)$$

where $$\frac{\partial n}{\partial T}$$

is the thermo-optic coefficient of the fiber and $\eta$ is the mode overlap factor. Equation (9) represents the optical space domain reflectometry (OSDR) signal for the multilayered structure, with the term in the bracket { ... } in Equation (9) being denoted as "$q_{osdr}$" herein.

Figures 3A, 3B:
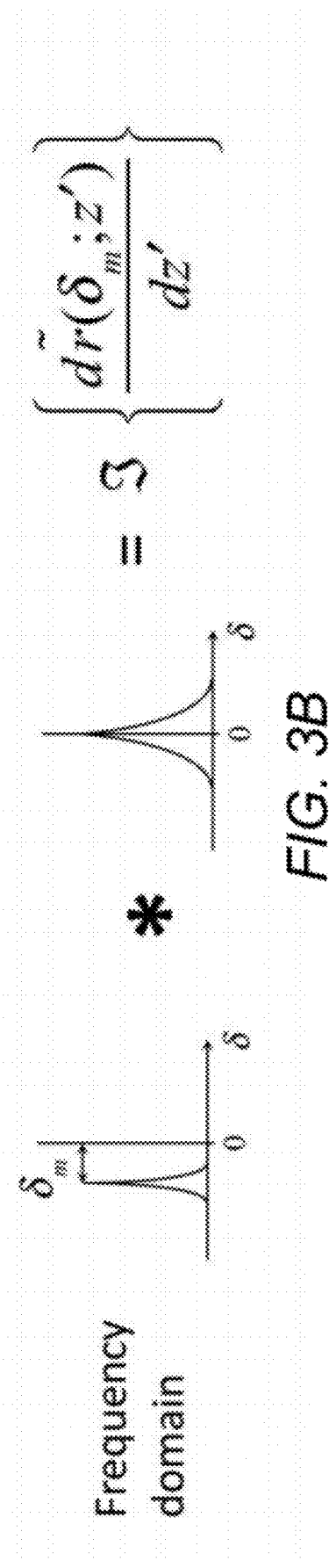
FIG. 3A depicts aspects of an optical space domain reflectometry (OSDR) signal which includes a coupling coefficient term $q_{osdr}$ in the spatial domain.
FIG. 3B illustrates aspects of a transformation of the term $q_{osdr}$ into the frequency domain.

The physical interpretation of the $q_{osdr}$ term can be better understood by transforming it from the spatial domain to the Fourier frequency domain, as illustrated in FIGS. 3A and 3B.

FIG. 3A shows the form of $q_{osdr}$ in the spatial domain shown in Equation (9) above, where the complex conjugate of coupling coefficient q(z), $q^*(z)\cdot\exp(2i\delta_m z)$, is convolved with the temperature perturbation term $\Delta T(-z)$, with the result being the reflected OSDR signal having a spatially varying complex reflectivity $$\frac{d\tilde{r}(\delta_m;z')}{dz'}.$$

FIG. 3B illustrates aspects of the transformation of $q_{osdr}$ into the frequency domain. As shown in FIG. 3B, from the frequency shifting property of the Fourier transform well known in the art, the term $\exp(2i\delta_m z)$ in the spatial domain acts to shift the Fourier spectrum of $q^*(z)$ by an amount equal to the measurement wavenumber detuning $\delta_m$. The spectrum that results is then multiplied by the spectrum of the heat perturbation $\Delta T(z)$, which acts as a spatial filter. Thus, this heat scan technique measures the coupling coefficient $q^*(z)$ filtered by the spectrum of the perturbation profile. Performing this measurement off-resonance acts to shift the spectrum of q(z) prior to the filtering process.

If the temperature profile is known, for example as described below, the temperature perturbation term $\Delta T(z)$ can be deconvolved from the reflected OSDR signal $q_{osdr}$, thus yielding the actual coupling coefficient of the grating.

Determining the temperature perturbation profile can be achieved by exposing a weak FBG to an incident beam such as a focused beam from $CO_2$ laser 113 shown in FIG. 1 and using optical frequency domain reflectometry and layer peeling to reconstruct the coupling coefficient of the perturbed and unperturbed FBG. This difference between the two yields the profile of the phase perturbation caused by the incident beam. The temperature perturbation profile can then be calculated using Equation (8), where $\phi_0(z)$ is the measured phase due to perturbation. See G. A. Cranch and G. A. Miller, "Improved implementation of optical space domain reflectometry for characterizing the complex coupling coefficient of strong fiber Bragg gratings" *Applied Optics*, Vol. 48, No. 22, pp. 4506-4513 (2009), the entirety of which is hereby incorporated by reference into the present disclosure.

Thus, in a first embodiment of the present invention, a multilayered periodic structure can be examined and evaluated after it has been inscribed by perturbing the structure using a temperature perturbation gradient $\Delta T(z)$, measuring the reflected OSDR signal $q_{osdr}$ of the periodic structure, and deconvolving $q_{osdr}$ from the temperature gradient.

It should be noted that a high-fidelity measurement of the reflected OSDR signal requires that the measurement wavenumber detuning $\delta_m$ be carefully chosen. Measurements of the OSDR signal taken at different values of $\delta_m$ will yield slightly different results, since $\delta_m$ will determine the amount by which the spectrum of $q^*(z)$ is shifted prior to filtering. For large $\delta_m$ values, the reflected OSDR signal $q_{osdr}$ will be highly attenuated due to the filtering effect of $\Delta T(z)$. In addition, measurement of strong gratings at small values of $\delta_m$ will not satisfy the Born approximation shown in Equation (4) while measurements taken with too large a phase perturbation $\phi_0(z)$ will not satisfy the implicit assumption of OSDR measurements (i.e. small $\phi_0$). Consequently, measurements made using a value of $\delta_m$ that does not satisfy these criteria will result in a poor signal-to-noise ratio leading to a noisy reconstructed coupling coefficient.

In a second embodiment of the present invention, a periodic multilayered structure can be monitored and evaluated in-situ as it is being formed layer-by-layer. In this embodiment, the complex reflectivity is measured and the complex coupling coefficient is calculated from this measurement as each layer is formed. The calculated value of the complex coupling coefficient can then be compared to a target value corresponding to an ideal error-free structure. This comparison can be performed by separating the complex coupling coefficient into its magnitude and phase components. The value of each component is compared to the magnitude and phase of the target coupling coefficient and the difference for each component is taken. If the difference in either case deviates from zero, then the coupling coefficient of the inscribed structure is deviating from the target structure. Integration of the difference signals yields error signals that can be fed back into the interferometer used to form the multilayered structure forcing this difference to equal zero. In a closed loop feedback system, these deviations can thus be prevented from building up so that the inscribed structure matches the target structure. In this way, the build-up of errors in the coupling coefficient of the structure, which can adversely affect performance, are prevented.

Figure 4:
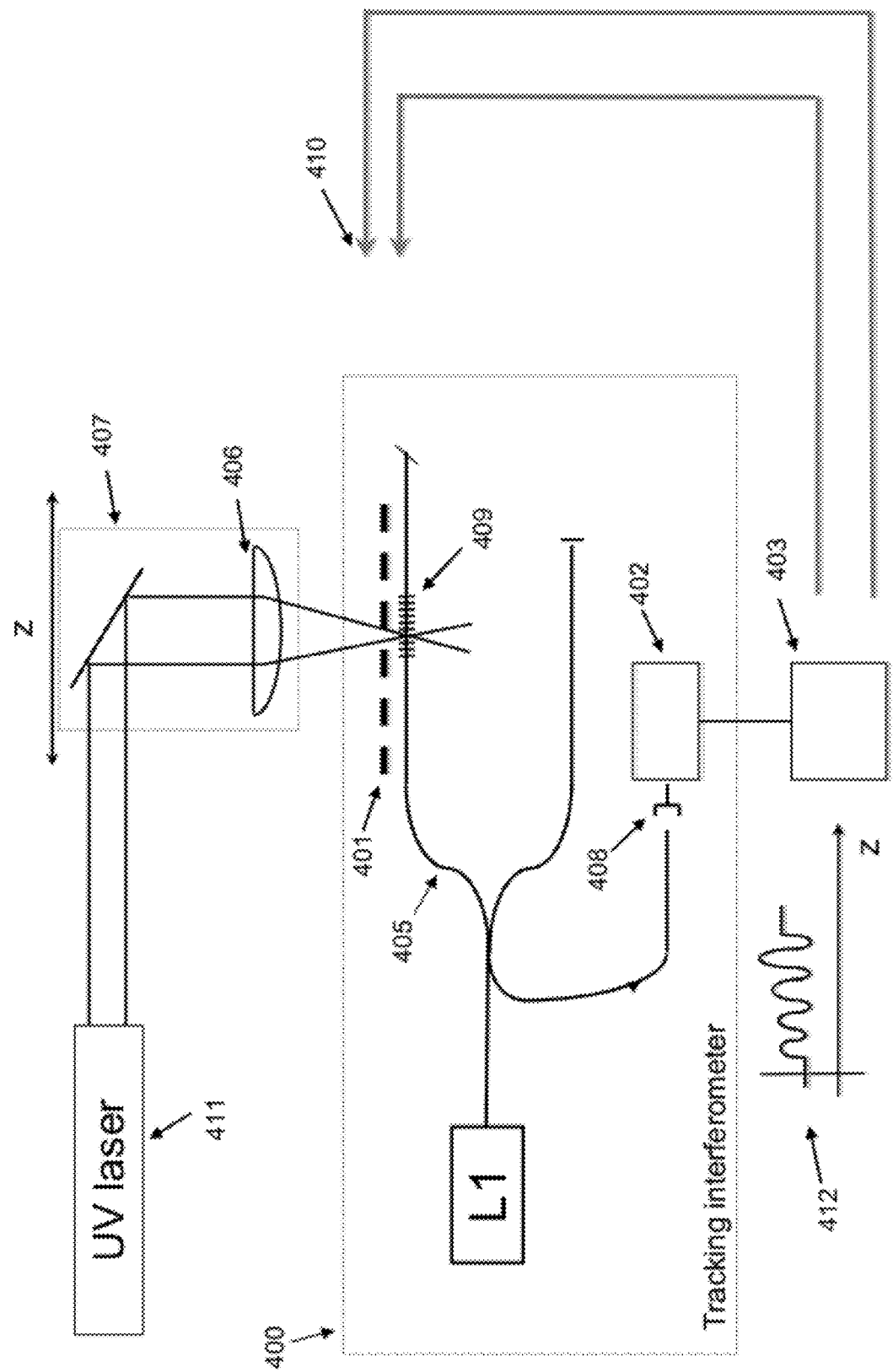
FIG. 4 depicts an exemplary embodiment of a closed loop inscription system for fabricating a multilayered structure in accordance with the present invention.

FIG. 4 illustrates a possible configuration of a closed loop system incorporating a tracking interferometer that can be used in accordance with the present invention.

As shown in FIG. 4, the multilayered structure is a fiber Bragg grating 409 along an optical fiber comprising arm 405 of the tracking interferometer 400. The output of a laser such as a UV laser 411 is focused through a lens 406 mounted on a translation stage 407. The translation stage 407 translates the UV beam across a phase mask 401 so that an interference pattern 412 is formed in the near field of the phase mask 401. The optical fiber is located within this UV interference pattern. The photosensitive effect in the optical fiber causes the refractive index n of the fiber to change in the presence of the UV fringe pattern such that a multilayered structure is formed in the optical fiber as a result of its illumination by the UV beam.

The change in refractive index of the optical fiber can be decomposed into two components, an ac refractive index, which represents the periodic modulation of the refractive index, and a dc component, which represents the background index. To those skilled in the art, it is well known that these two components can be independently controlled by applying motion to the phase mask. See M. J. Cole, W. H. Loh, R. I. Laming, M. N. Zervas and S. Barcelos, "Moving fibre/phase mask-scanning beam technique for enhanced flexibility in producing fibre gratings with uniform phase mask", *Electronics Letters*, Vol. 31, No. 17, pp. 1488-1490 (1995). The amplitude of the ac refractive index change in the fiber can be controlled by applying a dynamic dither to the phase mask through control of the amplitude of the dither. The phase of the ac refractive index change can be controlled by linearly translating the phase mask. The present invention therefore also provides a method of independently controlling both the amplitude and phase of the coupling coefficient of a multi-layered structure in an optical fiber by illuminating the fiber through a linearly translated phase mask.

As the UV beam is translated along the fiber, the interference pattern 411 measured on the photodiode 408 changes due to the change in the complex reflectivity of the multilayered structure. This change can be related to the local coupling coefficient at the current position of the UV writing beam. Thus, by decomposing this measured coupling coefficient into its magnitude and phase and taking the difference between these components and the magnitude and phase of the target coupling coefficient, deviations in the coupling coefficient of the multilayered structure from the target structure will yield non-zero values of these quantities. The interference pattern can be digitized, for example, by analog-to-digital converter 402 operationally coupled to photodiode 408, and the coupling coefficient and the comparison with the target structure can be performed by a computer such as computer 403. Integration of these quantities will yield two error signals 410 which can take the form of control voltages which can then be fed back into the interferometer to control the amplitude of the dither applied to the phase mask and the position of the phase mask.

It should be noted that other implementations for writing fiber Bragg gratings are possible and equally applicable to the present invention. For example, in one configuration, the UV beam is fixed and the fiber and phase mask are translated across the beam. See J. Martin, F. Ouellette, "Novel writing technique of long and highly reflective in-fibre gratings," *Electronics Letters*, Vol. 30, No. 10, pp. 811-812 (1994). In another configuration a UV interferometer is used to create a UV hologram in which the fiber is located. See, e.g., G. Meltz, W. W. Morey, W. H. Glenn, "Formation of Bragg gratings in optical fibers by a transverse holographic method," *Optics Letters*, Vol. 14, No. 15, pp. 823-825 (1989).

This embodiment of the present invention will now be described in the context of an exemplary configuration in which the multilayered periodic structure comprises an FBG written by translating a holographic fringe pattern formed by a UV laser along an optical fiber.

As described above, in accordance with the present invention, fabrication of such a multilayered periodic structure can be monitored by measuring the complex reflectivity of the grating at a value of measured wavenumber detuning $\delta_m$ corresponding to a region of weak interaction of the incident field with the periodic structure such that the Born approximation (Equation (4)) accurately relates the complex reflectivity $r(\delta)$ to the complex coupling coefficient $q(z)$. However, modeling the evolution of the complex reflectivity of a grating written layer-by-layer requires that a number of physical effects be accounted for, and a brief description of the physical processes involved will now be given.

The beam writing the FBG along the optical fiber can exhibit a spatial intensity profile $I(z)$, which is assumed to be a symmetric function centered about zero. The absorption of the UV light in the optical fiber results in at least two mechanisms which change the refractive index n of the illuminated region. These mechanisms can be categorized into a transient component and a non-transient component. The non-transient component persists when the UV beam is switched off and gives rise to the multilayered structure which, as explained above, can be described by its complex coupling coefficient q(z). The transient component is associated with a thermally induced change in the refractive index caused by a local heating of the fiber as the UV beam passes over it during the writing process. Real time measurement of the coupling coefficient will incorporate this transient component of the refractive index, which acts to perturb the phase of the measured complex coupling coefficient as the position of the UV beam changes. This thermally induced phase shift can be described by the function $\phi_{th}(z)$, which, as described above, can be related to the local temperature perturbation $\Delta T(z)$ using Equation (8). The thermally induced effect on the refractive index rapidly diminishes when the UV beam is switched off and thus can be treated separately from the permanent refractive index change giving rise to the grating structure.

In accordance with the present invention, a complex function which incorporates these physical effects can be used to determine the complex reflectivity at any point during the inscription procedure for the layer-by-layer writing approach. This function, denoted herein as A(z), is defined as $$|A(z)| = \begin{cases} 1 & z \leq 0 \\ \hat{I}(z) & z > 0, \end{cases}$$

where $\arg(A(z)) = -\phi_{th}(z)$ and $\hat{I}(z)$ is a normalized intensity function of the writing beam.

It should be noted that two assumptions have been made.

First, it is implicitly assumed that the permanent index change is linearly proportional to the beam intensity. Although this is often not the case, this discrepancy has little effect on the final measurement outcome. The reason for this is that the argument of the function A(z) dominates the behavior of the complex reflectivity due to the much larger spatial extent (~1 mm) of the transient component of the coupling component phase given by the function $\phi_{th}(z)$ compared with the half-width (~50-100 μm) of the beam intensity profile given by I(z). |A(z)| can thus be approximated to a unit step function. It is also known that in germanium doped silica fiber, initial exposure of the fiber to UV light at 244 nm causes a sudden increase in local coupling coefficient almost independent of UV intensity. Continued exposure of the fiber results in the coupling coefficient growth continuing with an approximately linear dependence on UV intensity. See, e.g., G. M. H. Flockhart, G. A. Cranch, and C. K. Kirkendall, "Rapid characterization of the ultraviolet induced fiber Bragg grating complex coupling coefficient as a function of irradiance and exposure time" *Applied Optics*, Vol. 46, No. 34, pp. 8237-8243 (2007) and G. A. Miller, C. G. Askins, G. A. Cranch, and E. J. Friebele "Early Index Growth in Germanosilicate Fiber Upon Exposure to Continuous-Wave Ultraviolet Light" *J. Lightw Tech*, Vol. 25, No. 4, pp. 1034-1044 (2007), both of which are incorporated by reference in their entirety into the present disclosure. The output of a real-time monitoring method of the type described below will result in an anomalously high initial signal due to this early growth behavior. However, this anomalous signal will rapidly disappear as the exposure progresses along the fiber. Optical fibers not exhibiting this so-called "early growth characteristic" may not exhibit this initial anomalous signal.

Second, it is assumed that the UV beam translates at a constant velocity v along the fiber, such that the position of the writing beam $z_2$ at time t from the beginning of the scan relative to the starting position $z_1$ can be expressed as $z' = (z_2 - z_1) = v \cdot t$.

Thus, given the above, the complex reflectivity $\tilde{r}(\delta_m; z')$ can be expressed in terms of the position of the beam along the optical fiber:

$$r(\delta_m; z') = -\int_{-\infty}^{\infty} q^*(z) \cdot \exp(2i\delta_m z) \cdot A(z - z') dz \quad (10)$$

We note here that it is not possible to further simplify Equation (10) using, for example, a small angle approximation for the phase shift $\phi_{th}(z)$ as was done for the post-inscription characterization method, since this phase shift can potentially be large depending on the absorption of the waveguide at the UV writing wavelength. Equation (10) can, however, be expressed in terms of a convolution as $$r(\delta_m; z') = -q^*(z) \cdot \exp(2i\delta_m z) \otimes A(-z) \quad (11)$$

In practice, however, it is more instructive to calculate the rate-of-change of $r(\delta_m)$, since for sufficiently small values of wavenumber detuning $\delta_m$ this is more closely related to q(z), and in fact is nearly proportional:

$$\frac{dr(\delta_m; z')}{dz'} = -q^*(z) \cdot \exp(2i\delta_m z) \otimes \frac{dA(-z)}{dz'} \quad (12)$$

A few observations reveal the elegance of the expression in Equation (12).

As explained above, the spatial extent (~1 mm) of the transient component of the coupling coefficient phase given by $\phi_{th}(z)$ greatly exceeds the half-width of beam intensity profile I(z) (~50-100 μm), and consequently, |A(z)| can be taken to be a Heaviside step function H with its axis reversed, i.e., H(−z). It would be readily appreciated by one skilled in the art that the function $A(z) = H(-z)\exp(-i\phi_{th}(z))$ rapidly attenuates the right hand side of Equations (11) and (12) for increasing values of $\delta_m$, causing a dramatic reduction in signal-to-noise ratio (SNR). Thus, there is an optimum value of $\delta_m$ that achieves a sufficiently high SNR while remaining within the weak interaction regime as required by the Born approximation.

A continuous measurement of $$\frac{dr(\delta_m; z')}{dz'}$$

yields a quantity closely related to q(z) from which an error signal can be derived. It has been previously suggested that so long as $\delta_m$ is chosen to be large, a slowly varying approximation can be used to directly relate $r(\delta_m; z')$ to q(z') for the case of apodized multilayered structures. See U.S. Pat. No. 7,194,163 and Stepanov, et al., supra. However, the above analysis illustrates that this will never be practically achievable due to the rapidly diminishing signal to noise ratio (SNR) for increasing $\delta_m$. Physically, the transient component of the refractive index change effectively apodizes the leading edge of the multilayered structure, dramatically reducing the level of the sidebands for large values of $\delta_m$ and hence reducing the SNR.

It also has been suggested that by measuring the complex reflectivity at two wavelengths at large values of $\delta_m$ located on either side of the Bragg resonance during the inscription procedure, the environmentally induced optical path length changes can be calculated and subtracted from one of the measurements of the complex reflectivity. See U.S. Pat. No. 7,194,163 and Stepanov, et al., supra. However, the analysis above shows that this type of measurement will not be possible since the SNR will be inadequate to perform a useful measurement of $r(\delta_m;z')$ at large values of $\delta_m$. Furthermore, the present method is fully generic and can be applied to any multilayered structure in contrast to the method presented in U.S. Pat. No. 7,194,163, which is limited to apodized structures.

It is important to note that both Equation (6) (post-inscription measurement) and Equation (11) (in-situ measurement during multilayered structure inscription) show that measurement of the evolution of the complex reflectivity of the periodic structure yields an expression consisting of the complex coupling coefficient of interest convolved with a function related to the temperature perturbation in the optical fiber. In each case, the coupling coefficient can thus be extracted by deconvolving the complex reflectivity and the temperature perturbation function. However, in the case of in-situ measurement during inscription, simple calculation of the rate of change of the complex reflectivity can yield an expression closely related to the coupling coefficient, without the need for deconvolution. This is because in most practical cases the second term in Equation (11), $A(-z)$, is well approximated by a unit step function, such that the second term on the right-hand-side in Equation (12) is a Dirac delta function. Thus, Equation (12) reduces to $$\frac{dr(\delta_m;z')}{dz'} \simeq -q^*(z) \cdot \exp(2i\delta_m z)$$

This dramatically simplifies the calculation of the coupling coefficient because the spatial beam intensity profile does not need to be known. Instead, the coupling coefficient can be calculated directly from the measured complex reflectivity.

As described above, the present invention also includes an apparatus that can be used to monitor and evaluate a multilayered periodic structure in accordance with the methods described above. The apparatus can take the form of a tracking interferometer which can be used to measure and monitor the complex coupling coefficient of a multilayered periodic structure.

Figure 5:
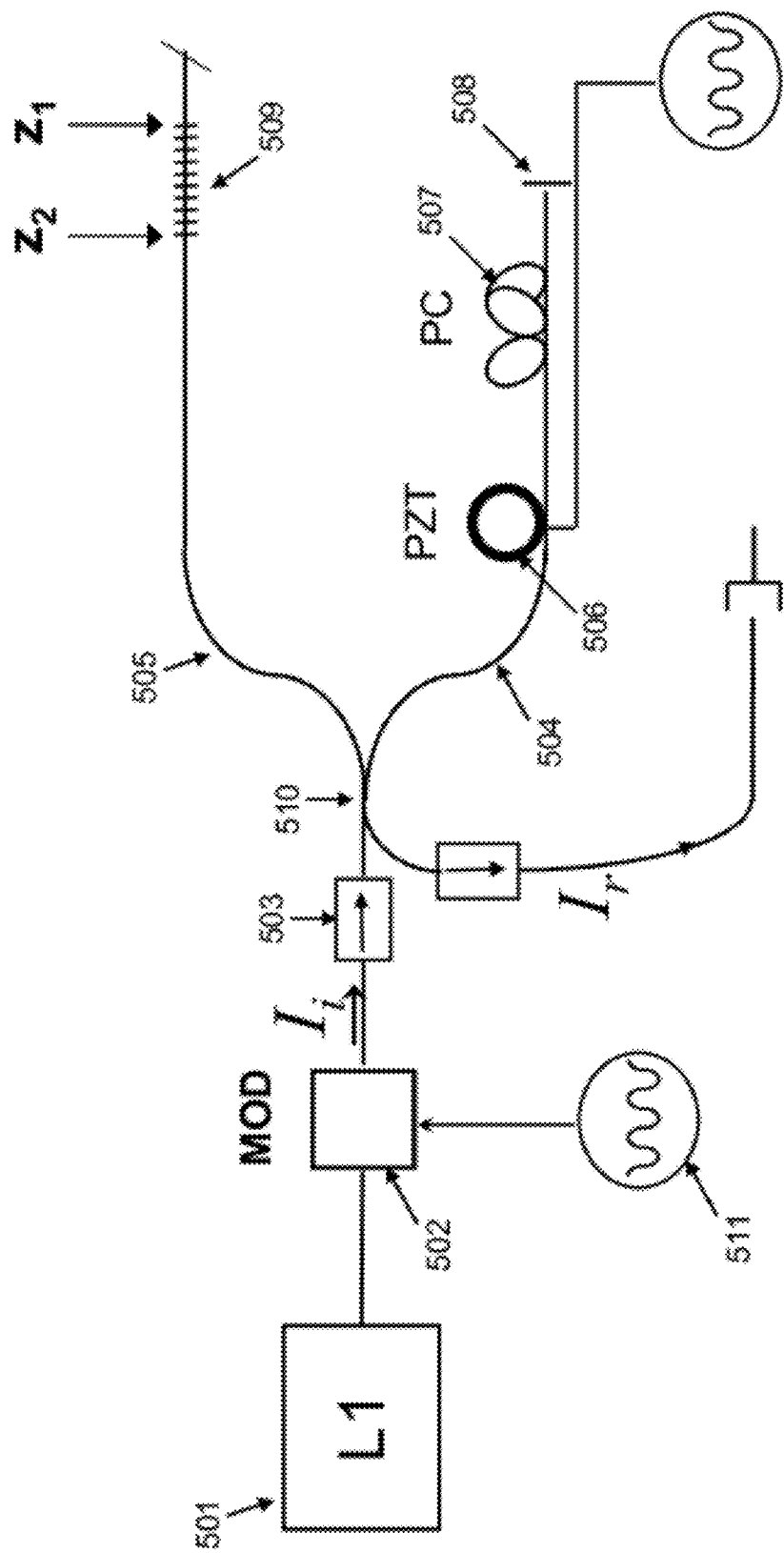
FIG. 5 depicts an exemplary embodiment of a tracking interferometer which can be used to measure and monitor the complex coupling coefficient of a multilayered structure in accordance with the present invention.

One exemplary embodiment of such a tracking interferometer comprises the Michelson interferometer arrangement illustrated in FIG. 5.

In the exemplary configuration shown in FIG. 5, the interferometer is illuminated by an optical signal having wavelength L1 generated by laser 501 which is passed through a high-frequency phase modulator (MOD) 502. The output of the modulator is a signal having an intensity $I_i$ and is injected through an isolator 503 and a directional coupler 510 into the Michelson interferometer (MI). In the configuration illustrated in FIG. 5, the MI has two arms 504 and 505, each comprising an optical fiber. Arm 504 of the MI is the reference arm and contains a low-frequency phase modulator, such as a fiber-wrapped piezo-electric tube (PZT) 506 and a polarization controller 507. The end of the arm 504 is terminated with a reflector 508 which reflects the signal back through arm 504 to generate reflected signal having an intensity $I_r$ which is then output by the MI.

The multilayer periodic structure 509 being evaluated is located on arm 505. The Multilayered structure 509 is located such that there is approximately zero optical path imbalance in the optical path between directional coupler 510 and structure 509 and the optical path between directional coupler 510 and reflector 508 to minimize conversion of source frequency noise to amplitude noise and permit upconversion of noise associated with parasitic cavities formed by backreflection from fiber terminations and components such as isolators (ISO).

Phase modulator 502, which is placed at the input to the interferometer, applies a high frequency (e.g. 15 MHz) phase modulation 511 to the input beam from laser 501 with a large modulation depth (e.g. >>1 rad). By phase modulating the input beam, the noise generated from parasitic cavities having a nonzero effective optical path imbalance can be upconverted around harmonics of this modulation frequency, which is far from the modulation frequency used by typical interferometric phase carrier or stepping methods (e.g. ~15 kHz). This yields a measurement resolution fundamentally limited by Rayleigh scattering only from the region of fiber containing the multilayered structure. The remaining fiber end from the multilayered structure is index matched to suppress any reflection. A polarization controller (PC) 507 is placed in arm 504 to allow the net birefringence of the interferometer to be minimized, yielding a high fringe visibility V. Perturbation of the input lead to the interferometer may also cause undesirable fluctuations of the fringe visibility, if the net birefringence in the interferometer is not zero. This effect can be reduced by placing a temporal polarization scrambler (not shown) at the input to the interferometer. The low frequency phase modulator, e.g., PZT 506, provides a means to modulate the optical phase, allowing the phase of the interferometer to be tracked using standard phase carrier or phase stepping techniques. See A. Dandridge, A. B. Tveten, and T. G. Giallorenzi, "Homodyne demodulation scheme for fiber optic sensors using phase generated carrier," *IEEE Journal of Quantum Electronics*, Vol. 18, No. 10, pp. 1647-1653 (1982), incorporated by reference herein.

The reflected intensity $I_r$ of the signal output from the MI, assuming directional coupler 510 is evenly split (i.e., 50:50), is given by $$I_{r\_n}(\delta_n;z') = \frac{I_{i\_n}}{2} R_{ref} + \frac{I_{i\_n}}{2}|r(\delta_n;z')|^2 + VI_{i\_n}\sqrt{R_{ref}}|r(\delta_n;z')|\cos(\phi(z')) \quad (13)$$

where $I_{i\_n}$ and $I_{r\_n}$ are the incident and reflected intensity for wavelength n, $R_{ref}$ is the power reflectivity of the reference reflector, $\delta_n$ is the detuning corresponding to wavelength n, V is the fringe visibility, $\phi(z')$ is the interferometric phase which contains the phase information of the complex reflectivity and $$2V\frac{I_{i\_n}}{2}\sqrt{R_{ref}}|r(\delta_n;z')|$$

is the amplitude of the interference pattern which contains the amplitude of the complex reflectivity.

As noted above, this interference pattern may be digitized and recorded in a computer, either a computer operatively coupled to the apparatus or a separate computer that receives input of the digitized interference pattern from any suitable digital storage medium using any suitable input mechanism, and the processing steps described below may be carried out in such a computer.

The complex reflectivity can be expressed in terms of its magnitude and phase, i.e., $r(\delta_n;z')=|r(\delta_n;z')|\exp(i\phi_r(\delta_n;z'))$ such that $\phi_r(\delta_n;z')$ is the phase of the complex reflectivity.

As described above, the phase $\phi(z')$ measured by the tracking interferometer can be separated into two components such that $\phi(z')=\phi_r(z')+\phi_{env}(z')$ where $\phi_{env}(z')$ represents a phase drift due to environmental perturbations on the tracking interferometer. Over short time periods this contribution can be ignored. However, over long time periods this contribution can be large and must be compensated for as described below.

It is well known to those skilled in the art that the amplitude and phase of the measured interference pattern can be separated using standard phase carrier or stepping methods. See Dandridge, et al., supra.

Thus, by suitable calibration of the measured interference pattern, the amplitude of the complex reflectivity can be calculated from the amplitude of the interference pattern and the phase of the complex reflectivity can be obtained from the phase of the interference pattern. This calibration may be carried out, for example, by tuning the input beam laser L1 shown in the Figures to a sideband of the multilayered structure with a known reflectivity level, thus enabling the amplitude of the fringe pattern to be calibrated.

For the case of the first embodiment described above, (i.e. post-inscription characterization of a multilayered structure) in accordance with the present invention, a focused laser beam is scanned along the fiber as illustrated in FIG. 1. Absorption of this laser beam by the fiber causes a localized change in the temperature of the fiber and forms the heat perturbation described by $\Delta T(z)$. As described above, the effect of this perturbation is observed as a change in the complex reflectivity which can be measured from the interference pattern obtained using a tracking interferometer such as the tracking interferometer described above with respect to FIG. 1. In practical situations, the environmental phase shift $\phi_{env}$ varies slowly compared with the measurement time and thus its contribution has little effect on the measurement accuracy.

The variation in the complex reflectivity as a function of the position of the heat perturbation forms the signal given by Equation (6), and the spatial derivative of this signal forms the OSDR signal given by Equation (9). The temperature profile $\Delta T(z)$ can be independently calculated using Equation (8) as described above. The coupling coefficient can thus be calculated from the measured complex reflectivity and the temperature profile $\Delta T(z)$ using Equation (9).

For the case of the second embodiment of the present invention (i.e. in-situ characterization), a holographic fringe pattern can be translated along an optical fiber, for example, using UV laser 411 shown in FIG. 4. The holographic fringe pattern may be at a wavelength of 244 nm generated from a frequency doubled Argon laser and created with a UV interferometer or phase mask method. Other potential writing wavelengths include 193 nm, 266 nm and 488 nm depending on waveguide composition. A multilayered structure is inscribed in the fiber which is incorporated into the tracking interferometer described above, e.g., with respect to FIG. 4. The complex reflectivity of this multilayered structure changes the interference pattern generated by the tracking interferometer, which, as described above, can be recorded in a computer.

As with the post-inscription characterization described above, the phase $\phi(z')$ measured by the tracking interferometer can be separated into two components such that $\phi(z')=\phi_r(z')+\phi_{env}(z')$ where $\phi_{env}(z')$ represents a phase drift due to environmental perturbations on the tracking interferometer. In most cases, the environmentally induced phase shift $\phi_{env}(z')$ can be reduced by environmental isolation, but it cannot be eliminated since the time required to inscribe a multilayered structure and hence the measurement time can be long. However, if the environmental phase shift is small, then the phase and amplitude of the complex reflectivity can be calculated from the interference pattern in accordance with Equation (13) and the coupling coefficient of the grating at the current position of the UV beam can be calculated using Equation (12).

Figure 6:
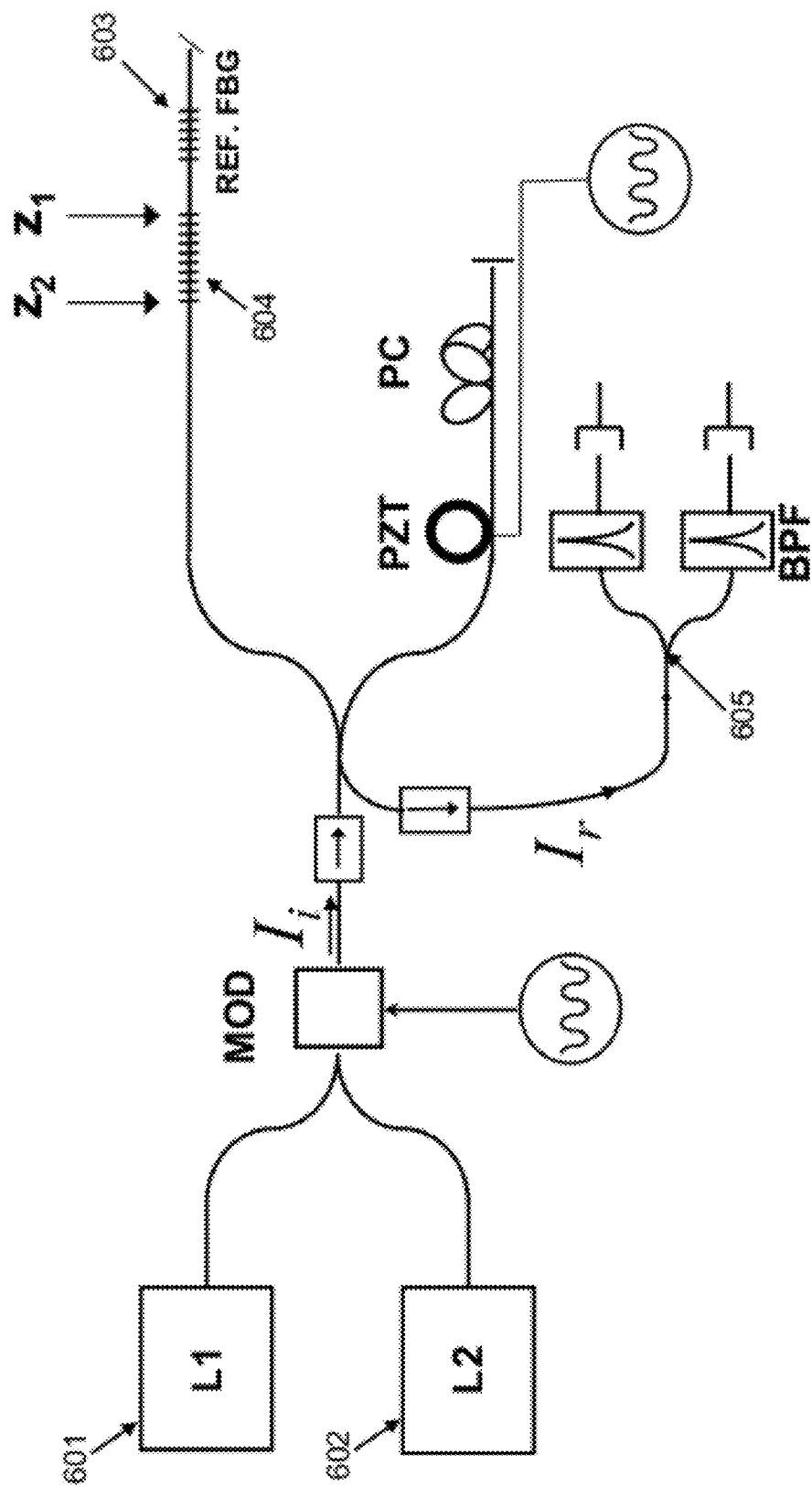
FIG. 6 depicts another exemplary embodiment of a tracking interferometer which can be used to measure and monitor the complex coupling coefficient of a multilayered structure in accordance with the present invention.

In many practical cases, however, the environmental phase shift $\phi_{env}(z')$ can be very detrimental since it can vary at the same rate as the phase of the complex reflectivity $\phi_r(z')$. Thus, a means of compensating for this environmental phase shift is necessary. One potential method for temperature compensation is used in the alternative embodiment illustrated in FIG. 6. As illustrated in FIG. 6, a second multilayered structure, identified in FIG. 6 as REF. FBG 603, can be located close to the multilayered structure to be tested 604. The reference structure is designed to interact with the incident optical signal radiation at a different wavelength than the structure under test. For example, the reference structure can be a Bragg grating with a center wavelength of 1310 nm. Similar to the embodiment shown in FIG. 5, in the embodiment shown in FIG. 6, an optical signal having a first wavelength L1 is input into the interferometer from laser 601. However, in the embodiment shown in FIG. 6, a second optical signal having a second wavelength L2 is also input into the interferometer from laser 602, with L2 separated from L1 at the output with an optical band pass filter (BPF) 605. Wavelength L2 generates its own interference pattern, the phase of which is affected only by environmental fluctuations. Thus, the measured environmentally induced phase $\phi_{env}(z)$ can be subtracted from the measured phase of the interference pattern of the multilayered structure 604 under test, leaving only the phase term $\phi_r(z')$ associated with the complex reflectivity of the multilayered structure.

Figure 7:
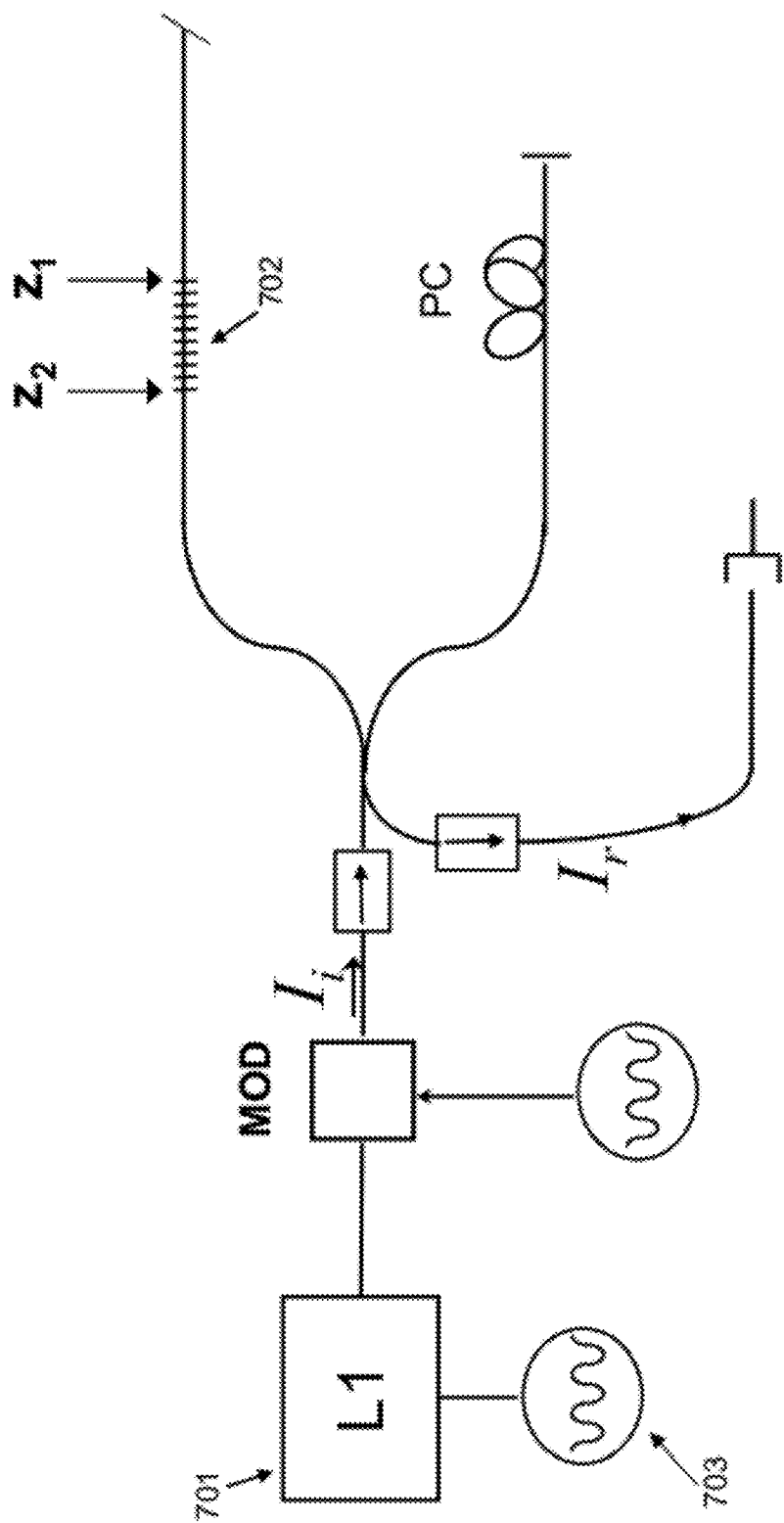
FIG. 7 depicts another exemplary embodiment of a tracking interferometer which can be used to measure and monitor the complex coupling coefficient of a multilayered structure in accordance with the present invention.

Another potential embodiment of a tracking interferometer that can be used in accordance with the present invention is shown in FIG. 7. In this embodiment, the tracking interferometer has essentially the same structure as that described above with respect to FIG. 5, but in this embodiment, the multilayered structure under test 702 can be placed at a location having a predetermined non-zero optical path difference and a phase generated carrier method can be implemented by placing a high-frequency optical modulator 703 to frequency modulate the laser source 701. See Dandridge et al., supra. In such a configuration, the modulation depth of laser 701 can be set to correspond to this path imbalance such that only the signal corresponding to the periodic structure is modulated onto the phase-generated carrier signal, while signals due to Rayleigh scattering and parasitic cavities (which correspond to different optical path imbalances) are upconverted outside the signal bandwidth. In this configuration, it may be necessary to frequency stabilize the lasers by, for example, locking them to an atomic absorption line or reference cavity.

Figure 8:
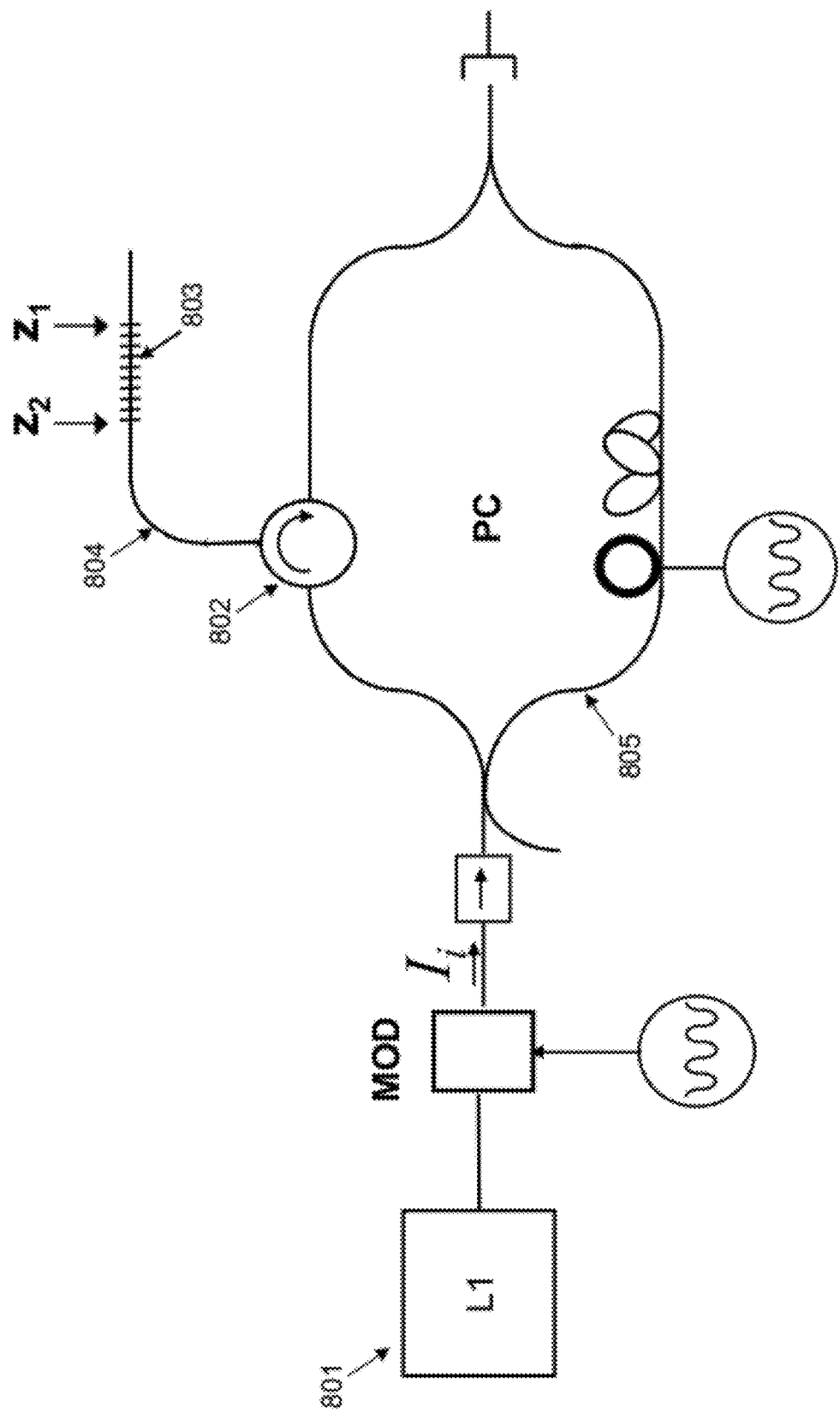
FIG. 8 depicts another exemplary embodiment of a tracking interferometer which can be used to measure and monitor the complex coupling coefficient of a multilayered structure in accordance with the present invention.

The embodiments of the invention described above are based on a Michelson interferometer. However, the concepts described above can be used with other interferometric measurement configurations such as the exemplary Mach-Zehnder interferometer configuration shown in FIG. 8. The Mach-Zehnder interferometer shown in FIG. 8 operates similarly to the way in which the Michelson configuration shown in FIG. 5 operates, with an optical signal from laser 801 being input into the interferometer and an interference signal created by the multilayered periodic structure being tested 803 which is on one arm 804 of the interferometer. However, in the Mach-Zehnder configuration, a circulator 802 couples the light reflected from the multilayered structure 803, and the reflected light is coupled back into the Mach-Zehnder interferometer having reference arm 805. The Mach-Zehnder interferometer shown in FIG. 8 is balanced when the optical path of the light interacting with the grating is matched to the optical path of the light passing through the reference arm. The analysis of the incident and reflected light is performed in the same manner as described above with respect to the Michelson interferometer, and so this configuration can also be used to track the complex reflectivity of a multilayered periodic structure in accordance with the present invention.

As noted above, one or more aspects of a method for monitoring and evaluating a multilayered periodic structure in accordance with the present invention can be accomplished by one or more computers either separate from or operatively connected to a tracking interferometer as described herein and which can receive digitized data of the interference pattern generated in an optical fiber as described above and execute one or more sequences of one or more computer-readable instructions read into the computer's memory. Such computer-readable instructions can be read from volatile or non-volatile computer-readable media capable of storing and/or transferring computer programs or computer-readable instructions for execution by one or more computers. Such volatile computer-readable media can include a memory such as a dynamic memory in a computer, while non-volatile media can include a compact disk, hard disk, floppy disk, tape, magneto-optical disk, PROM (EPROM, EEPROM, flash EPROM), SRAM, SDRAM, or any other magnetic medium; punch card, paper tape, or any other physical medium such as a chemical or biological medium.

Although particular embodiments, aspects, and features have been described and illustrated, it should be noted that the invention described herein is not limited to only those embodiments, aspects, and features. It should be readily appreciated that modifications may be made by persons skilled in the art, and the present application contemplates any and all modifications within the spirit and scope of the underlying invention described and claimed herein. For example, although particular configurations of tracking interferometers are illustrated and described, other configurations are possible, and any suitable configuration can be used. Also, although reference is made herein to $CO_2$ and UV lasers, one skilled in the art would appreciate that other lasers may be available and use of such other lasers may be used as is suitable. These and other such alternative embodiments are also contemplated to be within the scope and spirit of the present disclosure.

What is claimed is:

1. A method for characterizing a multilayered periodic structure in an optical fiber in-situ during its formation, comprising:

illuminating the optical fiber with a first optical signal, the optical fiber forming part of an interferometer wherein the first optical signal is reflected in the optical fiber, the reflected first optical signal being received by a photodiode;

illuminating the optical fiber with a second linearly translatable optical signal through a phase mask, the second optical signal causing a perturbation in the fiber which changes a refractive index in the fiber at a point of illumination by the second optical signal, a multilayered periodic structure being formed layer-by-layer by successively illuminating portions of the optical fiber with the second optical signal through the phase mask, wherein at each point in its formation the multilayered periodic structure has an associated complex reflectivity as a function $r(\delta_m; z')$ of a perturbation position $z'$ along a length of the multilayered periodic structure and a measurement wavenumber detuning $\delta_m$ such that the reflected first optical signal has an interference pattern on the photodiode caused by the complex reflectivity of the multilayered periodic structure, a value of the complex reflectivity being determinable from the interference pattern;

determining $$\frac{dr(\delta_m; z')}{dz'},$$

a spatial rate of change of the complex reflectivity of the multilayered periodic structure, after each successive layer is formed;

deriving a complex coupling coefficient $q^*(z)$ of the multilayered periodic structure from the value of $$\frac{dr(\delta_m; z')}{dz'}$$

as each successive layer is formed, wherein $q^*(z)$ is approximately equal to $$\frac{dr(\delta_m; z')}{dz'}$$

by the relation $$\frac{dr(\delta_m; z')}{dz'} \simeq -q^*(z) \cdot \exp(2i\delta_m z);$$

comparing the derived complex coupling coefficient $q^*(z)$ to a target complex coupling coefficient associated with a target multilayered periodic structure to determine a difference between the extracted coefficient and the target coefficient; and adjusting the formation of the next layer of the multilayered structure if the difference between the derived coefficient and the target coefficient is not zero.

2. The method for characterizing a multilayered periodic structure in an optical fiber according to claim 1, further comprising:

calculating an error signal if the difference between the derived coefficient and the target coefficient is not zero; and changing at least one of an amplitude of a dither applied to the phase mask and a position of the phase mask in response to the error signal to adjust the formation of the next layer of the multilayered periodic structure.

3. The method for characterizing a multilayered periodic structure according to claim 1, wherein the second optical signal comprises a focused beam from a UV laser.

4. The method for characterizing a multilayered periodic structure according to claim 1, wherein the multilayered periodic structure is a fiber Bragg grating.

5. The method for characterizing a multilayered periodic structure according to claim 4, wherein the measurement wavenumber detuning $\delta_m$ is far from a Bragg resonance of the multilayered periodic structure.

6. The method according to claim 1, further comprising deriving the relation $$\frac{dr(\delta_m; z')}{dz'} \simeq -q^*(z) \cdot \exp(2i\delta_m z)$$

from the relation $$\frac{dr(\delta_m; z')}{dz'} = -q^*(z) \cdot \exp(2i\delta_m z) \otimes \frac{dA(-z)}{dz'},$$

wherein $$\frac{dA(-z)}{dz'}$$

is a Dirac delta function.

7. An apparatus for characterizing a multilayered periodic structure in an optical fiber in-situ during its formation, comprising:
a fiber-optic interferometer having a first arm comprising the optical fiber having the multilayered periodic structure being characterized inscribed therein and having a second arm comprising a reference optical fiber terminating in a reflector;
the first and second arms being joined by a directional coupler;
the multilayered periodic structure comprising a plurality of successively formed layers and being located so as to have a predetermined non-zero imbalance in an optical path between the directional coupler and the multilayered periodic structure in the first arm and an optical path between the directional coupler and the reflector in the second arm;
the multilayered periodic structure forming an interferometric cavity having an associated complex reflectivity;
a first optical signal source, the first optical signal source providing a first optical signal into the interferometer which is reflected and received at a photodiode, an interference pattern of the reflected signal on the photodiode being caused by the complex reflectivity of the multilayered periodic structure, a value of the complex reflectivity being determinable from the interference pattern; and
a second optical signal source, the second optical signal source causing a perturbation along the multilayered periodic structure, the perturbation changing the refractive index and the complex reflectivity of the perturbed multilayered periodic structure at each perturbation position such that the complex reflectivity of the perturbed multilayered periodic structure is a function $r(\delta_m; z')$ of a perturbation position $z'$ and a measurement wavenumber detuning $\delta_m$, the change in complex reflectivity being detected by a change in the interference pattern received at the photodiode;

wherein a complex coupling coefficient $q^*(z)$ can be derived from a spatial rate of change $$\frac{dr(\delta_m; z')}{dz'}$$

of the complex reflectivity of the perturbed multilayered periodic structure as each successive layer is formed along a length of the multilayered periodic structure, $q^*(z)$ being approximately equal to $$\frac{dr(\delta_m; z')}{dz'}$$

by the relation $$\frac{dr(\delta_m; z')}{dz'} \simeq -q^*(z) \cdot \exp(2i\delta_m z); \text{ and}$$

wherein the value of the derived complex coupling coefficient $q^*(z)$ is associated with at least one characteristic of the multilayered periodic structure.

8. The apparatus according to claim 7, further comprising a phase modulator placed at the input of the interferometer to implement phase generated carrier demodulation.

9. The apparatus according to claim 8, wherein the interferometer comprises a Mach-Zehnder interferometer.

10. The apparatus according to claim 7, wherein the second optical signal source comprises a laser and wherein the laser is directly modulated to implement phase generated carrier demodulation.

11. The apparatus according to claim 10, wherein the interferometer comprises a Mach-Zehnder interferometer.

12. The apparatus according to claim 7, further comprising a polarization scrambler placed at the input to the interferometer.

13. The apparatus according to claim 7, wherein the first optical signal source causes a temperature perturbation in the periodic structure, the apparatus further comprising a reference multilayered periodic structure close to the multilayered periodic structure being characterized, wherein the reference multilayered periodic structure is used for temperature compensation.

14. The apparatus according to claim 7, further comprising a high frequency optical modulator placed at the input of the interferometer to upconvert signals corresponding to parasitic cavities and stray reflections.

15. The apparatus according to claim 7, wherein the second optical signal source comprises a UV laser which exposes the fiber to an interference pattern through a phase mask, causing a permanent change in the refractive index of the fiber.

16. The apparatus according to claim 7, wherein the frequency of the first signal source is directly modulated to cause upconversion of the noise associated with parasitic cavities.

17. The apparatus according to claim 7, further comprising a polarization scrambler placed at the input to the interferometer.

18. The apparatus according to claim 7, wherein the relation $$\frac{dr(\delta_m; z')}{dz'} \simeq -q^*(z) \cdot \exp(2i\delta_m z)$$

is derived from the relation $$\frac{dr(\delta_m; z')}{dz'} = -q^*(z) \cdot \exp(2i\delta_m z) \otimes \frac{dA(-z)}{dz'},$$

wherein $$\frac{dA(-z)}{dz'}$$

is a Dirac delta function.

* * * * *